(12) United States Patent
Shah et al.

(10) Patent No.: US 11,877,882 B2
(45) Date of Patent: Jan. 23, 2024

(54) RESPIRATORY GATING USING PULSE OXIMETERS FOR TOMOGRAPHIC IMAGING

(71) Applicant: KONINKLIJKE PHILIPS N.V., Eindhoven (NL)

(72) Inventors: Kushal Shah, Mayfield Heights, OH (US); Andriy Andreyev, Willoughby Hills, OH (US); Shushen Lin, Cleveland, OH (US); Bin Zhang, Pittsburgh, PA (US); Chuanyong Bai, Solon, OH (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 979 days.

(21) Appl. No.: 16/605,867

(22) PCT Filed: Apr. 17, 2018

(86) PCT No.: PCT/EP2018/059703
§ 371 (c)(1),
(2) Date: Oct. 17, 2019

(87) PCT Pub. No.: WO2018/192890
PCT Pub. Date: Oct. 25, 2018

(65) Prior Publication Data
US 2020/0037976 A1 Feb. 6, 2020

Related U.S. Application Data

(60) Provisional application No. 62/488,186, filed on Apr. 21, 2017.

(51) Int. Cl.
*A61B 6/00* (2006.01)
*A61B 6/03* (2006.01)
*A61B 5/1455* (2006.01)

(52) U.S. Cl.
CPC ............ *A61B 6/5288* (2013.01); *A61B 6/037* (2013.01); *A61B 6/461* (2013.01); *A61B 6/527* (2013.01);
(Continued)

(58) Field of Classification Search
None
See application file for complete search history.

(56) References Cited

U.S. PATENT DOCUMENTS

2008/0281186 A1* 11/2008 Kuhara ................. A61B 5/055
600/413
2010/0290683 A1* 11/2010 Demeester ........... A61B 6/5288
382/131
(Continued)

OTHER PUBLICATIONS

International Search Report and Written Opinion of PCT/EP2018/059703, dated Jun. 29, 2018.
(Continued)

*Primary Examiner* — Serkan Akar
*Assistant Examiner* — Farouk A Bruce

(57) ABSTRACT

A device (10) for measuring respiration of a patient includes a positron emission tomography (PET) or single photon emission computed tomography (SPECT) imaging device (12). At least one electronic processor (16) is programmed to: extract a first respiration data signal (32) from emission imaging data of a patient acquired by the PET or SPECT imaging device; extract a second respiration data signal (36) from a photoplethysmograph (PPG) signal of the patient; and combine the first and second extracted respiration data signals to generate a respiration signal (40) indicative of respiration of the patient.

19 Claims, 2 Drawing Sheets

(52) U.S. Cl.
CPC ............ *A61B 6/5217* (2013.01); *A61B 6/582* (2013.01); *A61B 5/14552* (2013.01)

(56) References Cited

U.S. PATENT DOCUMENTS

| | | |
|---|---|---|
| 2011/0074409 A1 | 3/2011 | Stoughton |
| 2013/0085375 A1 | 4/2013 | Hamill |
| 2013/0211235 A1 | 8/2013 | Stoughton |
| 2014/0275832 A1* | 9/2014 | Muehlsteff ........... A61B 5/6889 600/301 |

OTHER PUBLICATIONS

Bundschuh, Ralph A. et al."Postacquisition Detection of Tumor Motion in the Lung and Upper Abdomen using List-Mode PET Data: A Feasibility Study", The Journal of Nuclear Medicine, vol. 48, No. 5, May 2007.

Leonard, P. et al., "Standard Pulse Oximeters can be used to Monitor Respiratory Rate", Emerg. Med J, vol. 20, pp. 524-525, 2003.

* cited by examiner

… (1) …

RESPIRATORY GATING USING PULSE OXIMETERS FOR TOMOGRAPHIC IMAGING

CROSS-REFERENCE TO PRIOR APPLICATIONS

This application is the U.S. National Phase application under 35 U.S.C. § 371 of International Application No. PCT/EP2018/059703, filed on Apr. 17, 2018, which claims the benefit of U.S. Provisional Patent Application No. 62/488,186, filed on Apr. 21, 2017. These applications are hereby incorporated by reference herein.

FIELD

The following relates generally to the vital sign monitoring arts, respiratory gating arts, medical imaging arts, image motion correction arts, and related arts.

BACKGROUND

The ability to reliably detect patient's respiratory motion and patterns is of great value in tomographic imaging to improve image quality. With the advancement in time of flight resolution (TOF) and computation capacity, the data-driven motion tracking algorithms have grown relatively mature for commercial use. The feasibility to detect respiratory motion with list-mode PET data has been shown [Bundschuh et. al., "Postacquisition Detection of Tumor Motion in the Lung and Upper Abdomen Using List-Mode PET Data: A Feasibility Study", J. Nucl. Med. 2007; 48:758-763]. The method of Bundschuh et al. detects movement of a lesion with focal uptake in the PET list mode data by tracking movement of the z-coordinate of the center-of-mass of the lesion activity distribution. The approach is applicable to post-acquisition list-mode data for detection of both periodic respiratory motion and irregular motion.

However, it is more challenging to track respiratory motion in real-time when the tomographic signal yields to low count statistics, which is often the case for clinical PET in which the radiopharmaceutical dose is kept low to limit radiation exposure of the patient. Insufficient sampling can result since the list mode data acquisition time for tracking respiration is inherently limited by the breath interval, which in turn introduces higher noise. Attempting to increase acquisition time degrades the temporal resolution to the motion signal.

The following discloses new and improved systems and methods to overcome these problems.

SUMMARY

In one disclosed aspect, a device for measuring respiration of a patient includes a positron emission tomography (PET) or single photon emission computed tomography (SPECT) imaging device. At least one electronic processor is programmed to: extract a first respiration data signal from emission imaging data of a patient acquired by the PET or SPECT imaging device; extract a second respiration data signal from a photoplethysmograph (PPG) signal of the patient; and combine the first and second extracted respiration data signals to generate a respiration signal indicative of respiration of the patient.

In another disclosed aspect, a non-transitory storage medium storing instructions readable and executable by an electronic processor operatively connected with an emission imaging device and a pulse oximeter to perform a respiration monitoring method is provided. The method includes: acquiring emission imaging data from the emission imaging device; acquiring a photoplethysmograph (PPG) signal from the pulse oximeter; generating an emission data driven respiration signal from the emission imaging data; generating a PPG-driven respiration signal from the PPG signal; determining a time shift of the PPG-driven respiration signal based on comparison of the PPG-driven respiration signal and the emission data driven respiration signal; and generating a respiration signal as the PPG-driven respiration signal shifted in time to correct for the determined time shift.

In another disclosed aspect, a device for measuring respiration of a patient includes an imaging device configured to obtain emission imaging data of at least a portion of a patient. A pulse oximeter is operably connected to a portion of a patient. The pulse oximeter is configured to obtain a photoplethysmograph (PPG) signal of the patient. At least one electronic processor is programmed to: extract a first respiration data signal from the emission imaging data; extract a second respiration data signal from the PPG signal; determine a time lag of the second respiration data signal respective to the first respiration data signal; and generate a respiration signal as the second respiration data signal shifted in time to correct the determined time lag. A display is configured to display the respiration signal of the patient.

One advantage resides in providing a system to measure respiratory activity during an image acquisition procedure.

Another advantage resides in improving the signal to noise ratio of PET acquired data.

Another advantage resides in determining the time lag in a plethysmograph (PPG) signal.

Another advantage resides in measuring a PPG signal of a patient during an image acquisition procedure without attaching bellows to the patient.

Another advantage resides in providing reliable real time respiratory gating signal.

Another advantage resides in generating substantially motion free images using respiratory gating operations.

Another advantage resides in utilizing patient's vital information obtained from PPG in addition to derived gating signal to develop a more intelligent motion correction algorithm.

A given embodiment may provide none, one, two, more, or all of the foregoing advantages, and/or may provide other advantages as will become apparent to one of ordinary skill in the art upon reading and understanding the present disclosure.

BRIEF DESCRIPTION OF THE DRAWINGS

The disclosure may take form in various components and arrangements of components, and in various steps and arrangements of steps. The drawings are only for purposes of illustrating the preferred embodiments and are not to be construed as limiting the invention.

DETAILED DESCRIPTION

Figure 1:
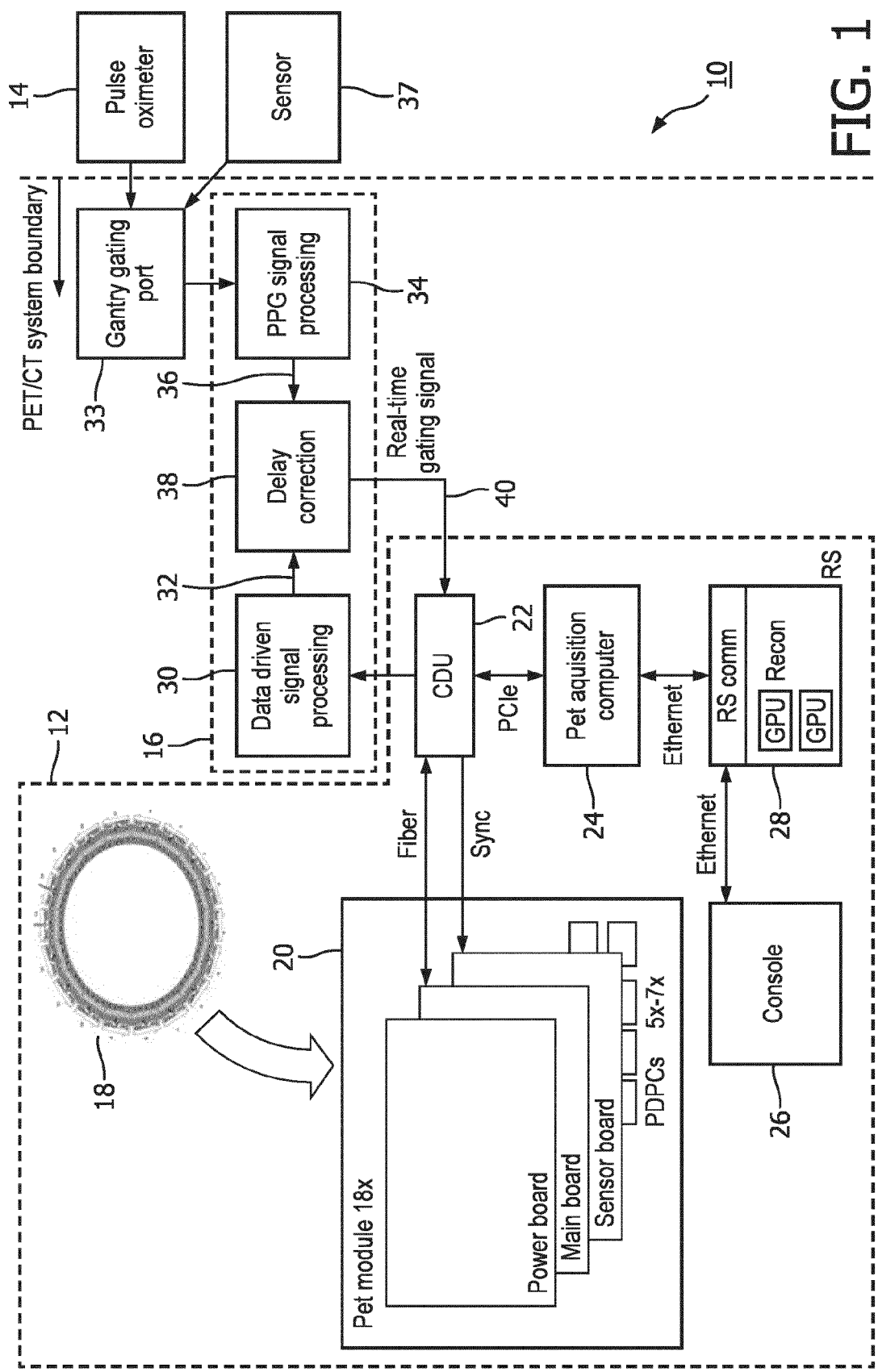
FIG. 1 diagrammatically shows a device for measuring respiration of a patient according to one aspect.

As discussed previously, data driven respiratory monitoring by analysis of the PET list mode data can provide real-time respiration cycling information without the need for the patient to wear a respiratory monitoring belt, but the approach is limited in accuracy and reliability by low count rates in clinical PET imaging of human subjects.

Pulse oximetry can be used to continuously monitor the oxygenation of hemoglobin by using the light absorption properties of oxygenated and deoxygenated blood. It has also been shown that pulse oximeters can be used for respiratory gating. Patients' respiratory rate can be determined by performing wavelet signal analysis on the photoplethysmogram (PPG) [Leonard et. al, Emerg. Med. J. 2003; 20:524-525]. Advantageously, the PPG signal is not limited by radiopharmaceutical dose, and generally provides a respiratory signal with higher signal to noise ratio (SNR) than the respiratory signal derived from clinical PET list mode data by data driven approaches. Furthermore, a pulse oximeter is compatible with the PET imaging environment, and is sometimes already used for monitoring blood oxygenation during PET imaging.

However, it is recognized herein that performing respiratory monitoring using the PPG signal acquired by pulse oximetry has a substantial problem, namely that there can be a significant time lag between the respiratory motion signal and the PPG. This time lag is believed to be attributable to finite transit time of respiratory-induced fluctuations from the core body region (i.e. torso) to the finger or foot where the pulse oximeter is typically attached. This delay, which varies from patient to patient and even may change over time for a given patient, makes the PPG signal (by itself) impractical for real time respiratory gating of PET imaging.

As already noted, a major disadvantage of data-driven methods is that signal reliability depends on the radiopharmaceutical dosage and count statistics. Gating errors become more likely in the cases of low radiation dosage due to insufficient sampling. Another disadvantage lies in high computational burden of the data-driven methods. However, data-driven methods operating on the PET list mode data have the advantage of being inherently real-time, as they directly detect respiration-induced motion of the lesion or other imaging feature of interest.

The following discloses a synergistic combination, namely using a pulse oximeter to perform respiratory gating in tomographic imaging by performing signal processing and analysis of plethysmogram, in combination with correction of any time lag between the respiration and the PPG signal using data driven analysis of the PET list mode imaging data. This enables use of the PPG and its typically high SNR for the gating, while overcoming the primary difficulty of PPG-based respiratory gating, namely the uncertain time lag. Moreover, using a pulse oximeter, not only can the respiratory rate for gating be obtained, but optionally also patient's vital parameters and pathology information. Analysis of plethysmogram by wavelet transform enables rapid detection of changes in breathing patterns allowing for corrections for apnoea or bradypnoea. The motion signal from plethysmograms provides reliable information about the patients' breathing pattern during tomography scan. Using approaches disclosed herein, the major drawback of the timing delay between actual blood oxygenation and respiratory cycle due to the time needed for oxygenated portion of blood to reach the pulse oximeter location is overcome, enabling PPG to be used for real-time respiratory gating of PET imaging.

In disclosed approaches, the data-driven motion gating method provides a real-time reference for the pulse oximeter signal and enables plethysmograms to be analyzed along acquisition of tomographic data. Comparing the data-driven motion signal with pulse oximeter signal can also discern the irregular pulmonary movement with higher confidence. Overall, using data-driven respiratory signals to correct the delay in pulse oximeter signal allows for more accurate respiratory motion tracking while significantly simplifying the patient-preparation protocol.

The following discloses solutions to several important issues in the field of medical imaging to provide reliable and robust respiratory gating, while relaxing the need for high count statistics (often unattainable in clinical radioemission imaging due to patient radiation exposure limits) or the use of complex and cumbersome external devices such as respiration monitor belts. The following discloses overcoming the shortcomings of above methods to provide a real-time respiratory gating signal by temporally aligning the pulse oximeter respiratory signal with the data-driven signal using advanced signal processing. Once the delay between pulse oximeter signal and patient breathing pattern is known the computationally expensive data-driven signal processing can optionally be stopped and the gating may rely on oximeter measurements alone.

The disclosed improvement synergistically combines two respiratory monitoring techniques: data driven respiratory monitoring by PET; and respiratory monitoring using a pulse oximeter. The PET based approach monitors real-time PET counts in the area of the lung/diaphragm interface. The oscillating movement of PET activity in the axial or z-direction (for a prone or supine patient) as "seen" in the real-time PET is indicative of respiratory movement, with the position corresponding to smallest lung size correlating with end-exhalation (since the lungs are thereby mostly emptied of air).

Respiratory monitoring by pulse oximetry is based on frequency composition (e.g. as extracted by wavelet analysis) of the plethysmograph. It is expected that the component of the plethysmograph at the frequency corresponding to the respiratory rate is due to respiration.

Each of the constituent respiratory monitoring techniques has deficiencies when used for respiratory gating of PET imaging. The PET data driven approach has poor signal-to-noise ratio (SNR) due to the low 511 keV count rate for real patients administered a low dose of radiopharmaceutical. This makes the monitoring spotty sometimes, with gaps in the reliable data stream due to noise when the count level is very low. The problem is made worse with larger-girth patients who absorb/scatter a greater fraction of the 511 keV emissions.

Monitoring by pulse oximetry usually provides much higher SNR and can provide a continuous data stream with few or no gaps, making it well-suited for real-time respiratory monitoring for PET respiratory gating. The pulse oximeter is also a small device, typically worn on a fingertip, and thus is more comfortable for the patient and presents little gamma ray absorption/scattering when compared with a bellows-based respiratory monitor. Moreover, the pulse oximeter provides useful vital sign data including pulse rate and oxygen saturation ($SpO_2$) level), hence a pulse oximeter may already be used during the PET imaging for these purposes. However, the respiratory signal provided by the plethysmograph of pulse oximetry has the disadvantage of having a substantial time lag, which is believed to be due to a transit time of blood flow (or of pressure waves passing through the blood flow) on the order of one second to a few seconds from the sourcing torso to the finger.

The disclosed improvement combines these two respiratory monitoring techniques as follows. Both are performed simultaneously, and during time intervals over which the PET data driven approach gives reliable data (in spite of its low SNR), it can be correlated with the respiratory component of the plethysmograph, so as to empirically measure the time lag of the respiratory component of the plethysmograph. With this time lag known, the plethysmograph can be used to provide real-time respiratory gating. Both signals can be continuously monitored throughout the PET imaging procedure so as to update the time lag value over the course of the PET imaging in case it varies over time (or, in an alternative embodiment the data driven signal is acquired only initially to determine the time lag of the PPG signal).

In one variant approach, an initial time lag calibration is performed using intentionally introduced "deep breaths" or other patient-controlled respiratory features to assist in the calibration. In another variant approach, some prior information, such as pulse rate, respiratory cycle, or so forth, may be used to improve the respiratory signal extraction from the pulse oximeter signal.

With reference to FIG. 1, an illustrative device 10 for measuring respiration of a patient is shown. As shown in FIG. 1, the device 10 includes a positron emission tomography (PET) imaging device 12, although another suitable emission imaging device may be used (e.g., a single photon emission computed tomography (SPECT) imaging device). The PET imaging device 12 is configured to acquire imaging data of at least a portion of a patient. The device 10 also includes a pulse oximeter 14 that is operably connected to a portion of the patient. The pulse oximeter 14 is configured to obtain a photoplethysmograph (PPG) signal of the patient. In a typical configuration, the pulse oximeter includes red and infrared LEDs, lasers, or other light sources that illuminate a volume of tissue (e.g. a fingertip or toe). The difference in absorption of the respective red and infrared light by oxygenated versus deoxygenated blood provides the basis for extraction of blood oxygen saturation. Additionally, the PPG signal cycles with heart pulsations enabling extraction of a heart rate, and can also be leveraged to extract respiration information, e.g. as described in Leonard et. al, Emerg. Med. J. 2003; 20:524-525. (As recognized herein, however, the respiration signal derived from the PPG may in general have some time lag when compared with the real-time cycling of the lungs.) The pulse oximeter 14 is shown diagrammatically in FIG. 1, but is typically configured as a clamp-on device that can be clamped onto a finger, toe, earlobe, or the like, with the light sources arranged on the clamp housing to illuminate the clamped finger et cetera and photodetectors arranged on the clamp housing to detect light after passing through the finger et cetera. The device 10 further includes at least one electronic processor 16 programmed to generate a respiration signal of the patient from the imaging data and the PPG signal, as described in more detail below.

As shown in FIG. 1, the PET imaging device 12 includes components typically known in the art of PET devices (as diagrammatically depicted by the bolded dashed box). For example, the PET imaging device 12 includes a gantry 18 with a plurality of detector modules 20 disposed thereon, with one detector module 20 diagrammatically shown in FIG. 1. The detectors 20 are configured to detect counts along lines of response (LORs) imaging data, with each count produced by two oppositely directed 511 keV gamma rays emitted by a positron-electron annihilation event, and this data is transmitted to a coincidence detection unit (CDU) 22. Each count is time stamped with its time of detection to create list mode data. The CDU 22 is connected to a PET acquisition computer 24 by any suitable means (e.g., an Ethernet connection, a Peripheral Component Interconnect Express (PCIe), and the like). The PET acquisition computer 24 accumulates a list mode data set which is reconstructed by a Reconstruction System (RS) 28 with graphical processing units (GPUs) or other suitable computational units that reconstruct the PET imaging data using a suitable iterative image reconstruction technique (e.g. MLEM, OSEM, et cetera). The reconstructed PET image may be displayed on a console 26 or otherwise utilized.

For prospective respiratory gated PET imaging, the data at the CDU 22 is filtered by respiratory phase, and only list mode data collected during a chosen phase (e.g. end-expiration) is reconstructed to form an image. This gating reduces motion artifacts due to respiration. An illustrative embodiment of respiratory gating using the disclosed synergistic combination of PPG and data driven respiration monitoring is next described.

The respiration monitoring employs data driven signal processing 30 operating on the list mode imaging data collected by the CDU 22 to generate a first respiration signal 32 (diagrammatically illustrated as an arrow in FIG. 1). In a suitable embodiment, the data-driven signal processing 30 detects movement of a lesion with focal uptake (or, alternatively, movement of some other image feature forming a "hot spot" in the PET list mode data) by tracking movement of the z-coordinate of the center-of-mass of the lesion activity distribution. See, e.g. Bundschuh et. al., "Postacquisition Detection of Tumor Motion in the Lung and Upper Abdomen Using List-Mode PET Data: A Feasibility Study", J. Nucl. Med. 2007; 48:758-763. Advantageously, this approach does not require computationally costly reconstruction of the list mode imaging data to generate a reconstructed image, and accordingly can be performed in (essentially) real-time to provide the first respiration signal 32 in real time. Moreover, since the data driven signal processing 30 is monitoring movement of the lesion in the torso as it moves with inhalation and exhalation, the first respiration signal 32 has substantially no time lag respective to the respiratory cycling. It is also straightforward to map the z-coordinate of the lesion activity center of mass to the actual breathing phase based on physiological first principles: at end-inhalation the lungs are maximally filled with air so that the lesion is moved maximally to the caudal direction; whereas, at end-exhalation the lungs are maximally emptied so that the lesion is moved maximally to the cranial direction. Thus, the first respiration signal 32 is readily synchronized with the "ground truth" respiratory phase. However, the first respiration signal 32 is prone to noise and is likely to have a low SNR due to low count rates in the usual case of clinical imaging in which the patient is administered with a clinically permitted low dose of radiopharmaceutical.

The pulse oximeter 14 is connected to a portion of the patient when the patient is in the imaging device 12 to obtain a PPG signal of the patient. In the illustrative layout, the PPG signal is communicated to the electronic processor 16 performing the gating via a gantry gating port 33 which may employ a wired or wireless (e.g. Bluetooth™) connection. The pulse oximeter 14 is acquiring the PPG concurrently with acquisition of the PET imaging counts at the CDU 22. The at least one electronic processor 16 is programmed to perform PPG signal processing 34 to extract a second respiration signal 36 (diagrammatically illustrated as an arrow in FIG. 1) from the PPG signal. In a suitable embodiment, the PPG signal processing 34 extracts the second respiration signal 36 as a component of the PPG signal in a frequency range spanning the range of credible breathing rates, e.g. using a wavelet signal analysis performed on PPG signal. See, e.g. Leonard et. al, Emerg. Med. J. 2003; 20:524-525.

In some examples, at least one other vital sign sensor 37 (e.g., a cardiac sensor, a respiration sensor, and the like) may be connected to the patient to obtain additional vital sign data or information. In this example, the at least one electronic processor 16 is further programmed to extract the second respiration signal using the obtained vital sign information from the vital sign sensor 37 (e.g., by augmenting the strength PPG signal with the obtained vital sign data to "fill in" any gaps in the PPG signal, such as those due to noise). The pulse oximeter 14 is in communication with the at least one electronic processor 16 via a gating port 32 of the gantry 18 of the imaging device 12.

The at least one electronic processor 16 is further programmed to combine the first and second respiration signals 32, 36 by data processing 38 to generate a respiration signal 40 indicative of respiration of the patient. In one suitable approach, the data processing 38 determines a time lag or delay of the second respiration signal 36 compared with the first respiration signal 32, and shifts the second respiration signal 36 in time to correct for this time lag in order to generate the respiration signal 40. The resulting respiration signal 40 is suitably used as a real-time gating signal to select those counts collected by the CDU 22 that are time-stamped during a time interval corresponding to a desired respiratory phase (e.g. end-expiration), and only those counts collected during the target respiratory phase are communicated to the PET acquisition computer 24 for inclusion in the imaging data set that is reconstructed by the RS 28.

In a variant approach (not shown in FIG. 1), the gating respiration signal 40 is input to the PET acquisition computer 24, rather than to the CDU 22. In this approach, suitable for retrospective respiratory gating, all counts are passed from the CDU 22 to the PET acquisition computer 24 to form the imaging data set, and the selection of which portions of this imaging data set are input to the RS 28 for image reconstruction is determined retrospectively by the PET Acquisition Computer 24 comparing time stamps of the counts against the recorded gating respiration signal 40.

To generate the respiration signal from the first and second respiration data signals 32, 36, the data processing 38 performed by the least one electronic processor 16 is programmed to determine a time lag of the second respiration data signal 36 respective to the first respiration data signal 32. The time intervals of the imaging data are correlated with the respiratory component of the PPG signal to measure the time lag of the respiratory component. Once the time lag has been determined, the second respiration signal 36 is shifted in time to correct for the determined time lag, thus forming the respiration signal 40 used for the respiratory gating. In one example, the at least one electronic processor 16 is programmed to update the determined time lag using continuously acquired imaging data, and extracting the first signal therefrom. In another example, the at least one electronic processor 16 is programmed to determine an initial time lag value with intentionally-induced breaths by the patient. Once the respiration signal is generated, the at least one electronic processor 16 is programmed to use the respiration signal to perform respiratory gating operations on the emission imaging data using the respiration signal. The data from the gating operations are passed to the reconstructed images and is used to guide motion artifact correction to generate "motion free" images. In addition, the respiration signal is displayed on the CDU 22.

The electronic processor 16 which performs the respiratory monitor processing 30, 34, 38 can be variously embodied. In the illustrative example, the electronic processor 16 is a dedicated electronic processor that is separate from the computing components 22, 24, 28 of the PET imaging device 12. In another embodiment, one or more of these computing components 22, 24, 28 may be modified to perform the respiratory monitor processing 30, 34, 38, e.g. a single electronic processor may implement both the CDU 22 and the illustrated electronic processor 16.

Figure 2:
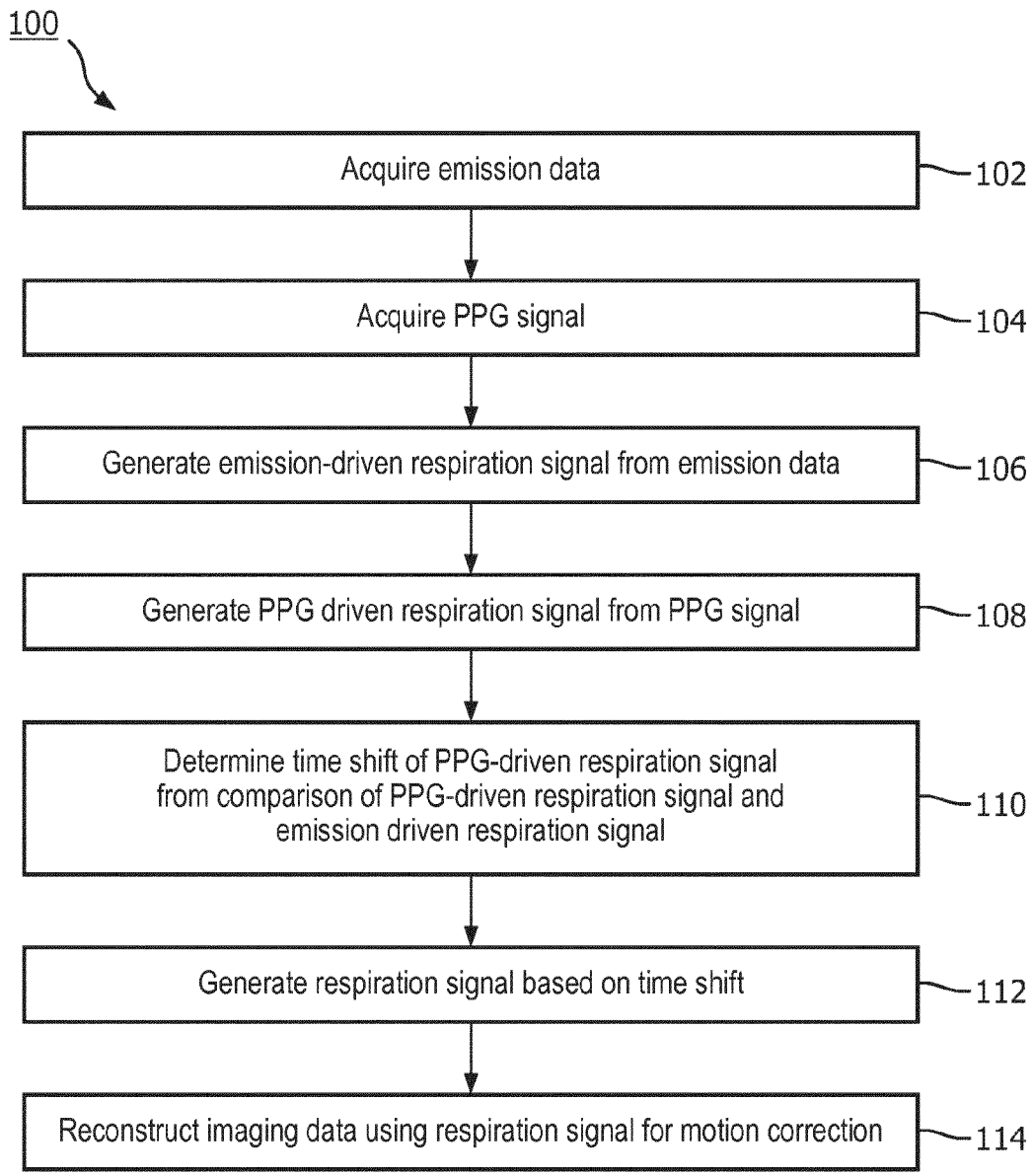
FIG. 2 diagrammatically shows an operational flow chart for operation of the device of FIG. 1.

With reference to FIG. 2, operation of the device 10 is diagrammatically flowcharted as a respiration monitoring method 100. At 102, emission data is acquired from emission imaging device 12. At 104, a PPG signal is acquired from the pulse oximeter 14. It will be appreciated that the operations of 102 and 104 may occur simultaneously or consecutively. At 106, at least one electronic processor 16 is programmed to generate an emission data driven respiration signal 32 from the emission imaging data. The emission data driven respiration signal is generated based on a position of an image feature as a function of time determined from the emission imaging data. In one example, the image feature comprises a lung/thoracic diaphragm interface of the patient. At 108, the at least one electronic processor 16 is programmed to generate a PPG-driven respiration signal 36 from the PPG signal. It will be appreciated that the operations of 106 and 108 may occur simultaneously or consecutively. At 110, the at least one electronic processor 16 is programmed to determine a time shift of the PPG-driven respiration signal 36 based on comparison of the PPG-driven respiration signal and the emission data driven respiration signal 32. In some examples, the determining of the time shift (at 108) and the generating of the respiration signal as the PPG-driven respiration signal shifted in time to correct for the determined time shift (at 110) is performed continuously or at successive time intervals during the acquiring of the emission imaging data. At 112, the at least one electronic processor 16 is programmed to generate a respiration signal 40 as the PPG-driven respiration signal 36 shifted in time to correct for the determined time shift. At 114, the at least one electronic processor 16 is programmed to reconstruct the emission imaging data using the generated respiration signal 40 to generate a reconstructed image. For example the reconstructed imaging data can be used for gating or motion correction, among other functions.

It will be appreciated that the illustrative computational, data processing or data interfacing components of the device 10 may be embodied as a non-transitory storage medium storing instructions executable by an electronic processor (e.g., the electronic processor 16) to perform the disclosed operations. The non-transitory storage medium may, for example, comprise a hard disk drive, RAID, or other magnetic storage medium; a solid state drive, flash drive, electronically erasable read-only memory (EEROM) or other electronic memory; an optical disk or other optical storage; various combinations thereof; or so forth.

The disclosure has been described with reference to the preferred embodiments. Modifications and alterations may occur to others upon reading and understanding the preceding detailed description. It is intended that the invention be construed as including all such modifications and alterations insofar as they come within the scope of the appended claims or the equivalents thereof.

The invention claimed is:

1. A device for measuring respiration of a patient, the device comprising:
   a positron emission tomography (PET) or single photon emission computed tomography (SPECT) imaging device; and
   at least one processor programmed to:

extract a first respiration data signal from emission imaging data of a patient acquired by the PET or SPECT imaging device;

extract a second respiration data signal from a photoplethysmograph (PPG) signal of the patient; and generate a respiration signal indicative of respiration of the patient, wherein generating the respiration signal comprises:

determining a time lag of the second respiration data signal respective to the first respiration data signal; and generating the respiration signal as the second respiration data signal shifted in time to correct the determined time lag.

2. The device of claim 1, wherein the first respiration data signal is extracted from the emission imaging data comprising data indicative of movement at a lung/diaphragm interface of the patient due to respiration.

3. The device of claim 1, wherein the at least one processor is further programmed to: perform respiratory gating of the emission imaging data using the respiration signal.

4. The device of claim 1, wherein the at least one processor is further programmed to: update the determined time lag using continuously-acquired emission imaging data.

5. The device of claim 1, wherein the at least one processor is further programmed to: determine an initial time lag value using induced breaths by the patient.

6. The device of claim 1, further comprising:

a vital sign sensor configured to obtain vital sign information of the patient, wherein the at least one processor is further programmed to extract the second respiration data signal from the PPG signal using the obtained vital sign information.

7. The device of claim 1, further including a display configured to display the respiration signal of the patient.

8. The device of claim 7, further comprising:

a pulse oximeter configured to acquire the PPG signal of the patient.

9. A non-transitory storage medium storing instructions readable and executable by a processor operatively connected with an emission imaging device and a pulse oximeter to perform a method of monitoring respiration of a patient, the method comprising:

generating an emission data driven respiration signal from emission imaging data;

generating a PPG-driven respiration signal from a photoplethysmograph (PPG) signal;

determining a time shift of the PPG-driven respiration signal based on comparison of the PPG-driven respiration signal and the emission data driven respiration signal; and generating a respiration signal as the PPG-driven respiration signal shifted in time to correct for the determined time shift.

10. The non-transitory storage medium of claim 9, wherein the emission data driven respiration signal is generated based on a position of an image feature as a function of time determined from the emission imaging data.

11. The non-transitory storage medium of claim 10, wherein the image feature comprises an interface between a lung and a thoracic diaphragm.

12. The non-transitory storage medium of claim 10, wherein the determining of the time shift and the generating of the respiration signal as the PPG-driven respiration signal shifted in time to correct for the determined time shift is performed continuously or at successive time intervals while acquiring the emission imaging data.

13. The non-transitory storage medium of claim 9, further storing instructions readable and executable by an electronic processor to reconstruct the emission imaging data to generate a reconstructed image.

14. A device for measuring respiration of a patient, the device comprising:

an imaging device configured to obtain emission imaging data of at least a portion of the patient; and at least one processor programmed to:

extract a first respiration data signal from the emission imaging data;

extract a second respiration data signal from a photoplethysmograph (PPG) signal;

determine a time lag of the second respiration data signal respective to the first respiration data signal; and generate a respiration signal as the second respiration data signal shifted in time to correct the determined time lag; and a display configured to display the respiration signal of the patient.

15. The device of claim 14, wherein the first respiration data signal is extracted from the emission imaging data comprising data indicative of movement at a lung and diaphragm interface of the patient due to respiration.

16. The device of claim 14, wherein the at least one processor is further programmed to:

perform respiratory gating operations on the emission imaging data using the respiration signal.

17. The device of claim 14, wherein the at least one processor is further programmed to:

update the determined time lag using continuously-acquired PET imaging data.

18. The device of claim 14, further including at least one other vital sign sensor configured to obtain vital sign information of the patient; and wherein the at least one processor is further programmed to extract the second respiration data signal from the PPG signal using the obtained vital sign information.

19. The device of claim 14, further including a pulse oximeter operably connected to a portion of a patient, the pulse oximeter being configured to obtain the PPG signal of the patient.

* * * * *